(12) United States Patent
Rodriguez et al.

(10) Patent No.: US 9,901,516 B2
(45) Date of Patent: Feb. 27, 2018

(54) PILL MANAGEMENT AND HEALTH MONITORING SYSTEM

(71) Applicant: Syntalli, Inc., Fort Lauderdale, FL (US)

(72) Inventors: Mark Rodriguez, Davie, FL (US); Carlos Reyes, Davie, FL (US)

(73) Assignee: Syntalli, Inc., Southwest Ranches, FL (US)

( * ) Notice: Subject to any disclaimer, the term of this patent is extended or adjusted under 35 U.S.C. 154(b) by 0 days.

(21) Appl. No.: 15/122,215

(22) PCT Filed: Feb. 23, 2016

(86) PCT No.: PCT/US2016/019205
§ 371 (c)(1),
(2) Date: Aug. 29, 2016

(87) PCT Pub. No.: WO2016/138047
PCT Pub. Date: Sep. 1, 2016

(65) Prior Publication Data
US 2017/0087059 A1    Mar. 30, 2017

Related U.S. Application Data

(60) Provisional application No. 62/119,473, filed on Feb. 23, 2015.

(51) Int. Cl.
*A61J 7/04* (2006.01)
*A61B 5/022* (2006.01)
(Continued)

(52) U.S. Cl.
CPC ............... *A61J 7/0481* (2013.01); *A61B 5/01* (2013.01); *A61B 5/022* (2013.01); *A61B 5/024* (2013.01); *A61B 5/14552* (2013.01); *A61J 7/0418* (2015.05); *A61J 7/0427* (2015.05); *G06F 19/3462* (2013.01); *H04N 7/147* (2013.01); *A61J 2200/30* (2013.01); *A61J 2205/10* (2013.01); *A61J 2205/60* (2013.01); *A61J 2205/70* (2013.01)

(58) Field of Classification Search
CPC ..................................................... A61J 7/0481
See application file for complete search history.

(56) References Cited

U.S. PATENT DOCUMENTS 5,826,217 A   10/1998   Lerner
6,294,999 B1   9/2001   Yarin et al.
(Continued)

OTHER PUBLICATIONS

Int'l Search Report and Written Opinion of PCT/US2016/019205, USA/ISA, dated May 2, 2016.

*Primary Examiner* — Gene O Crawford
*Assistant Examiner* — Stephen L Akridge
(74) *Attorney, Agent, or Firm* — Nancy J. Flint, Esq.; Nancy J. Flint, Attorney At Law, P.A.

(57) ABSTRACT

A system and method for the dispensing of medication in the form of pills and also to monitor health parameters is disclosed. The system comprises a modular system having a main control module; a plurality of pill dispensing modules in communication with the main control module; and optionally sensors to measure health parameters in communication with the main control module. The main control module can store information and also can communicate information over a communications network.

19 Claims, 10 Drawing Sheets

(51) Int. Cl.
*A61B 5/01* (2006.01)
*A61B 5/1455* (2006.01)
*A61B 5/024* (2006.01)
*G06F 19/00* (2018.01)
*H04N 7/14* (2006.01)

(56) References Cited

U.S. PATENT DOCUMENTS

| | | | |
|---|---|---|---|
| 8,483,872 | B2 | 7/2013 | Ratnakar |
| 8,878,654 | B2* | 11/2014 | Cohen-Alloro ..... G06F 19/3462 340/10.1 |
| 2002/0104848 | A1 | 8/2002 | Burrows et al. |
| 2004/0117062 | A1* | 6/2004 | Bonney ............. A61M 15/0045 700/237 |
| 2009/0167531 | A1* | 7/2009 | Ferguson ............ G06F 19/3462 340/572.1 |
| 2009/0281657 | A1 | 11/2009 | Gak et al. |
| 2013/0024022 | A1* | 1/2013 | Bowers ..................... A61J 1/03 700/236 |
| 2014/0042052 | A1* | 2/2014 | Tsai .......................... A61J 1/03 206/534 |
| 2014/0166529 | A1* | 6/2014 | Fung ........................ A61J 1/03 206/534 |

* cited by examiner

PILL MANAGEMENT AND HEALTH MONITORING SYSTEM

FIELD OF THE INVENTION

This application relates generally to a system and method for the dispensing of medication in the form of pills and also to monitor health parameters. The system comprises a modular system having a main control module; a plurality of pill dispensing modules in communication with the main control module; and optionally sensors to measure health parameters in communication with the main control module. In addition, the system can optionally obtain external sensor readings and also allow the user to manually enter health parameters.

The main control module can store information obtained internally, externally or entered by the user. The main control module also can communicate and receive information over a communications network in support of various tasks such as data transfer, notifications, system configuration, video conferencing, etc.

The main control module may further comprise a camera for use in video conferencing, and also to scan and OCR materials relating to medication as well as any other algorithms that would be beneficial to the user.

BACKGROUND OF THE INVENTION

While taking a particular medication on a regular schedule may seem a simple process for many people, it is often difficult to accomplish for others. For example, a patient that has been prescribed to take multiple prescription medications at different times can become confused. Some patients spend a lot of time measuring out medication, which is an opportunity for making an error. This can be particularly dangerous where medicines are not intended to be taken together due to adverse effects, or where the patient's condition makes him forgetful.

U.S. Pat. No. 8,896,428 titled MEDICINE DISPENSING RECORD SYSTEM and issued to Shalala, the content of which is herein incorporated by reference, discloses a dosage cap that records and displays dosage information about a medicine, including, the projected time that the next dosage of medicine is needed, the time interval between numerous administrations of the medicine, the time and/or date that the last dose was administered, the current daily intake amount, the date the dose was administered, or scheduled administration of the medicine. The time and date of the last dosage of medicine administered can be reset and updated when a subsequent dose of medicine is administered. The cap secures over a medicine container lid to provide easy visibility of the dosage information to a user. A shaft extends downwardly from the cap to secure the cap to the medicine container lid by penetrating the lid with a sharp point. A fastener attaches to the end of the shaft for securing the cap to the medicine bottle lid.

U.S. Patent Application Publication No. US 2002/0104848 titled PHARMACEUTICAL CONTAINER HAVING SIGNALING MEANS AND ASSOCIATED METHOD OF USE and issued to Burrows et. al., the content of which is herein incorporated by reference, discloses a container having signaling capability for use with medicine and other pharmaceutical related products. The container preferably includes a conventional bottle-type body with a rotatable secured closure. A sensor means is structured to determine the position of the closure and thereby provide an indication of cap rotation indicative of the patient using the medicine. A processing means and display means are also included in the container to provide an indication of the current state of the container with respect to its contents. In addition, the container can include a button means to permit a user of the container to scroll through indicia shown on the display means. In another aspect of the container, a base station is provided for transmitting data to/from a signal means incorporated into the container. The base station includes a body having at least one receptacle for suitably receiving a container therein.

U.S. Patent Application Publication No. US 2012/0316405 titled PORTABLE VITAL STATISTICS MONITORING AND MEDICATION DISPENSING SYSTEM and issued to Taylor, the content of which is herein incorporated by reference, discloses a portable vital statistics monitoring and medication dispensing system that provides personal healthcare management and daily prescription routines. The medication dispenser and vital statistics monitor combination incorporates a medication dispenser, a blood testing system, a pill cutting module operated by the control unit, and other vital sign monitoring into a portable wireless device with customizable features. The medication dispenser and vital statistics monitor combination has the capability of notifying the user of the correct times to take medication and automatically dispensing the accurate prescription dosage. The medication dispenser and vital statistics monitor combination communicates the patient information using an onboard display, transmits the information to a local or distributed network, or prints/embosses/etches the information onto patient information cards, wristbands, or other information sheets.

U.S. Pat. No. 7,715,277 titled INTERACTIVE MEDICATION CONTAINER and issued to De la Huerga, the content of which is herein incorporated by reference, discloses an interactive medication container or console that hold or otherwise organizes one or more medication vials or containers. Each vial has a memory strip containing medication and prescription information. Each vial can also include a reminder unit that is attached to and portable with the individual vials. The console or reminder unit reads the information strip of the vial and communicates this information to or interacts with a patient to remind them to take the medication. The medication container or reminder unit also gathers or tracks information such as consumption time, quantity remaining, patient feedback, and contraindication information. The medication container or reminder unit interacts with the patient by displaying questions or receiving and recording input from the patient before, during or after a dose of medication is taken. The patient input can be used to modify the dosing regimen for future doses of medication. The medication container reorders medication when the quantity remaining reaches a threshold level. Contraindication information in the memory strip is downloaded to a personal home computer or a hospital or nursing home computer.

U.S. Patent Application Publication No. US 2014/0166529 titled PILLBOX, MEDICATION MANAGEMENT SYSTEM AND MEDICATION DISPENSING SYSTEM and issued to Fung et.al., the content of which is herein incorporated by reference, discloses a pillbox comprising a plurality of pill receiving compartments detachably connected with one another in side-by-side relation to form a unitary structure, each of the compartments being constructed to store pills to be taken at a single predetermined time and have an opening which is covered by a cover and through which the compartment is accessible; wherein the unitary structure is configured such that the plurality of compartments are arranged sequentially according to a medication schedule created according to a prescription, with the compartment storing the pills to be taken first as an outermost one, and that only the opening of the outermost compartment is permitted to be uncovered all the time, and wherein the outermost compartment is removed from the unitary structure after the pills contained therein are taken. The invention also provides a medication management system and a mediation dispensing system based on the pillbox.

U.S. Patent Application Publication No. US 2009/0315702 titled MEDICATION DISPENSER issued to Alloro et.al., the content of which is herein incorporated by reference, discloses a method for providing medication according to a preset schedule, the method comprising: providing a disposable medication dispenser containing medication to a user; connecting one dispenser monitor to said medication dispenser; monitoring a state of said medication with said monitor; providing, via said monitor, signals with respect to said state of said medication to a health monitoring station; and monitoring the state of dispenser at the health monitoring station.

SUMMARY OF THE INVENTION

In operation, a user obtains a main control module and one or more pill box modules and/or health parameter sensor modules. The user connects the pill box modules and health parameter sensor modules to the main control module via a distributed power and communication system which allows for bi-directional communication between main control modules and the other modules via a wired communications link. The distributed power and communications system also provides for provision of power to the modules. In addition, the user obtains an external sensor with a communications link that interfaces with the main control module. Furthermore, the user defines a set of health parameters that can be manually entered and are stored in the memory of the main control module.

The user can configure the system directly from the main control module or by accessing the main control module from an external device. Configuration encompasses scheduling for medications contained in the pill box modules and also external medications not stored in a pill box module; the taking of readings from the health parameter sensor modules; the taking of readings from external sensors not physically connected to the system via a health parameter sensor module; and user input health parameters. The configuration also includes setting up notifications via a communications network.

In one embodiment, the pill box modules are each separately designated with unique identifiers by the programmable processor of the main control module. The user can program each pill box module from the main control module using an LCD display unit or by accessing the main control module from an external device. For example, the user can set the dosage schedule and dosage amount of the pills in each pill box module. The main control module transmits information regarding the dosage and dosage schedule to the respective pill box modules, where the information is stored in the programmable processor of the pill box modules. When the time for a dose arrives according to a clock in the main control module, a visual and/or audible alarm is given notifying the user of the pill box module(s) from which to take medicine. The pill box module associated with that dosage event can display on its LED display the number of pills to be taken, thus giving a visual display to take medication from that particular pill box module and also informing how many pills to take. The pill box module can detect if the module is opened and closed and transmit that information to the main control module where it can be stored and accessed to see if the user opened the pill box module at the dosage time. The pill box module can also contain a sensor that can detect when the pill box module is empty and provide an indicator that it needs to be refilled.

In one embodiment, the pill box module is supplied to the user filled with the medication and programmed as to the dosage schedule. When the pill box module is connected to the system, the main control module detects the presence of the pill box module and receives the information concerning dosage from that pill box module. The main control module creates a schedule for that pill box module and operates as previously described.

In one embodiment, the user can program an external medication(s) schedule and dosage from the main control module using the LCD display unit or by accessing the main control module from an external device. For example, the user can set the dosage schedule and dosage amount of external medication to be taken by the user. The main control module displays the information regarding the dosage and dosage schedule to the respective external medication. When the time for a dose arrives for an external medication according to a clock in the main control module, a visual and/or audible alarm is given notifying the user of the external medication to take along with the dosage. The user would confirm compliance directly from the main control module.

In one embodiment, one or more health parameter sensor modules can be attached to the system as are the pill box modules. Each health parameter sensor module is designed to read information regarding a particular health parameter. For example, a blood pressure health parameter sensor module is programmed to detect and transmit blood pressure information to the main control module. Many health parameter sensor modules require that an external sensor be attached to the module to detect the health parameter. For example, the blood pressure health parameter sensor module would provide a connection for a cuff.

As for the dosage schedules, the main control module may be programmed to remind the user to measure various health parameters. In addition, the health parameter sensor module is supplied to the user filled with the sensor information and programmed as to the monitoring schedule.

The various health parameter sensor modules are manufactured for use with their particular sensors and contain the programming needed to allow the user to operate the sensor. The main control module can receive and display usage information from the health parameter sensor modules as well as receive data. In one embodiment, the main control module identifies the particular health parameter sensor module. If a monitoring schedule is programmed into the health parameter sensor module, the main control module can download it and update the master schedule to reflect this sensor reading.

In one embodiment, the time for a reading from a health parameter sensor module arrives and the main control module provides a visual and/or audible alarm notifying the user. The main control module then requests the health parameter sensor module to obtain a reading from the user. The health parameter sensor module contains the programming and instructions on how to obtain the readings so it sends information to be displayed directly on the main control module display. The user then follows the instructions displayed in the main control module and completes the steps required to take the health parameter sensor module reading. The reading is then sent to the main control module where it is stored and displayed.

The main control module provides power to the health parameter sensor modules, but in some cases additional power may be needed in which case the particular health parameter sensor module can allow for input of external power.

In one embodiment, the time for a reading from an external sensor is transmitted by the external sensor to the main control module, which then provides a visual and/or audible alarm notifying the user. The user then links the external sensor through wired or wireless communication to the main control module. When the external sensor reading is obtained, the reading is transmitted to the main control module where it is stored and displayed.

In one embodiment, the time for a reading from a user defined input parameter arrives and the main control module provides a visual and/or audible alarm notifying the user. The user then obtains this defined parameter which can include external sensors (i.e. weight, pressure, heartrate, etc.) or other health parameters (i.e. height, skin color, presence of rash, emotional state, etc.)

By providing modular connectivity and bi-directional communication, the system is infinitely customizable for a user, and also easily changed according to the user's changing needs.

Thus, in addition to internal pill and external medication management, the system can support scheduling of a wide range of readings that include internal sensors, external sensors, user input parameters and other user reminders (i.e., to drink a glass of water).

In one embodiment, the pill box modules comprise two components: a pill box hub and a detachable pill box enclosure. The pill box hub comprises a display and the electronics required for operation of the pill box module. The pill box hub connects to the main control module via a distributed power and communication system which allows for bi-directional communication between main control modules and the other modules via a wired communications link in the same manner as the single component pill box module. The distributed power and communications system also provides for provision of power to the pill box hub. The pill box hub comprises an internal cavity to accommodate a pill box enclosure.

The pill box enclosure is an air tight compartment that accommodates medication in the form of pills. The pill box enclosure comprises an information storage device in the form of an RFID, barcode or similar technique/device that contains a unique identifier and additional information relating to the pills in the pill box enclosure, wherein the additional information may comprise the medicine name, dosing details or scheduling information. The pill box enclosure is inserted into the cavity of the pill box hub to form a pill box module.

DESCRIPTION OF THE DRAWINGS

The invention will be described with reference to the accompanying drawings, in which like elements are referenced with like numerals.

DETAILED DESCRIPTION OF THE INVENTION

Figure 1:
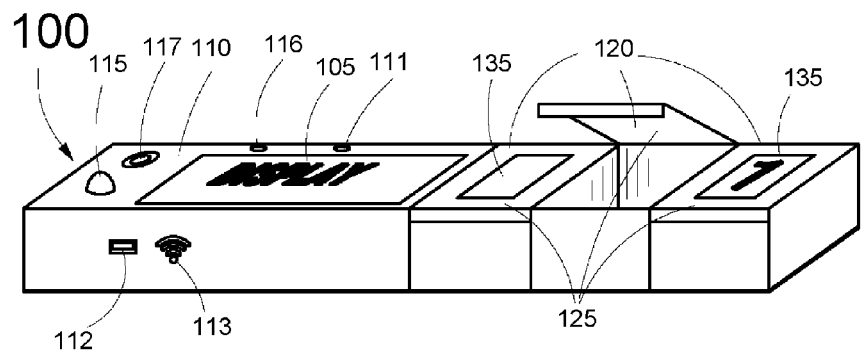
FIG. 1 depicts a system having a main control module and three pill box modules.

The Pill Management & Health Monitoring System (PM-HMS) comprises a system and method that enables a user to manage internal pill dispensing and optionally to monitor health parameters as well as external medication dosages and external health and user input parameters. The system comprises functionality to support pill management, health parameter monitoring, data aggregation and management, external device interface and notifications.

The system comprises a plurality of components including a main control module; a modular communication and power distribution unit; one or more pill box modules; one or more health parameter sensor modules; and optionally a portable control module.

In one embodiment, the PMHMS provides a system and method for users to easily manage dispensing of pills. It allows a user to track the correct medication, dosage and time for the taking of medication and/or supplements. The PMHMS does not require pill pre-sorting by the user since the system indicates to the user the time and dosage of the pills to take. The system is intended to function by allocating one type of medication per pill box module. The main control module can alert the user by an audible and/or visual alarm. The pill box module indicates to the user a pill to take and the quantity of the pills in each dosage. This combination provides an easy method of pill management which is also intuitive to the user. The PMHMS is modular so it can be configured by the user to accommodate the number of pills that need to be managed. In addition, if the number of pills changes, the PMHMS can easily be configured to accommodate an increase or decrease in the number of pills being managed. Furthermore, the PMHMS can support adding external medication management to incorporate the management of external medications, pills, supplements, etc.

The PMHMS can support health parameter monitoring by allowing health parameter sensor modules to be connected to the main control module. The PMHMS can accommodate a variety of health parameter sensor modules as needed and/or desired by the user. The PMHMS communicates with the health parameter sensor modules via a communications link. Furthermore, the system allows the user to enter health data (i.e., weight, height, temperature, etc.).

The PMHMS can support monitoring of pill box modules, health parameter sensor modules, external sensor data and user input data. These data are aggregated and managed by the main control module. The PMHMS can provide data and indications through visual display and/or audio visual indicators, and can store health data in memory internally from which data can be displayed.

The PMHMS comprises a communications link that can support external notifications to outside devices (i.e. phones, Internet, etc.). The PMHMS can support notifications and updates to other persons or entities associated with the user's health management. In addition, system data can be transmitted to an external location via this communication link. In one embodiment, the PMHMS links directly to pharmacies for automatic reordering of medication, receipt of instructions and alerts from a pharmacist, receipt of notifications that medication is ready for pick-up and/or receipt of discounts and coupons from the pharmacy.

In one embodiment, the PMHMS comprises an attached camera that includes software to scan medication information for entry of the medication information into the system memory. Medication information may be obtained from bottle labels, prescription information or any other format.

The camera may comprise a microphone and speaker that can support video conferencing functionality.

In addition to being modular, the system can also be expanded by having a separate and autonomous portable control module that can support pill box modules of a reduced size separate from the main control module. This portable control module can download the pill box schedule from the main control module and can operate without continuous connection to the main control module, but supports pill management activities locally. The portable control module is a reduced size control module that interfaces with the portable pill box modules. The portable pill box modules are pill box modules of reduced size compatible to the portable control module that retain the ability to display individual dosage. Once the portable control module is reconnected to the main control module, data can be transferred to the system to update the main control module. The portable system is similar to the PMHMS in operation while having a reduced physical profile.

Main Control Module.

The main control module performs multiple functions including providing a user interface to enter information into the PMHMS; providing a display data for the user; and providing visual and audible system indicators. The main control module further comprises a programmable processor that is configured to control scheduling and notification functions of the PMHMS, in addition to receiving and managing information from the pill box modules, the health parameter sensor modules and user data input.

The main control module provides programmable pill management which incorporates scheduling and control of the pill box modules as well as external medication or supplements that informs the user to when to take pills, the pill box module containing the pills and information about the dosage to take at a particular time, as well as when to take external medication or supplements along with the dosage of the external medication and supplements. The main control module further provides programmable management of health parameter sensor modules and external sensors that informs the user to take readings from either health parameter sensor modules or external sensors.

The main control module further supports modular communication and power distribution by which it provides power to the modules in the PMHMS and also establishes communications with the modules.

The main control module can download pill schedule data from any pill box module in the PMHMS and can also upload pill schedule data to any pill box module in the PMHMS. In addition, the main control module can send information (e.g. dosage number, flash number, etc.) and can also receive information (e.g. lid open/closed) from any pill box module in the PMHMS.

The main control module can further download sensor schedule data from any health parameter sensor module in the PMHMS and also upload sensor schedule data to any health parameter sensor module in the PMHMS. In addition, the main control module can send information (e.g. initiate reading, etc.) and receive information (e.g. display "Connect cuff", etc.) from any health parameter sensor module in the PMHMS. By receiving display messages from the health parameter sensor modules, the main control module display acts as a dumb terminal driven by the health parameter sensor modules. This allows the health parameter sensor modules to carry their individual "instructions for use" without the need to update the main control module software.

The main control module comprises a first communications link to external sensor devices that capture external sensor readings. The first communications link comprises a wired or wireless local area network (LAN) comprising a serial link, USB, Bluetooth, Ethernet, WiFi, Near field Communication, RF or any other type of communications protocol. The main control module may further communicate with PCs in support of PC based applications over the LAN.

In one embodiment, the main control module further comprises a second communications link to a wired or wireless wide area network (WAN) to transmit data to outside locations or devices and to be able to provide notifications to outside devices or locations.

In one embodiment, the programmable processor of the main control module further comprises an API that allows it to seamlessly interface to different pill box and/or health parameter sensor modules that are in communication over the modular communication bus. In addition, the main control module can support a separate API to support interfacing with external health parameter sensors via a communications link.

The main control module controls, interfaces and provides power to the various pill box and health parameter sensor modules that form the PMHMS. The main control module can be powered from an external DC source or an internal battery, and comprises complete internal clock capabilities for time tracking. The main control module is easily programmed by the user to set the time and quantity of dosing of pills contained in the separate pill box modules.

In one embodiment, the main control module also contains a built in camera, speaker and microphone that can support video conferencing.

The main control module can be programmed to report stored information to the user or any third party. For example, regular reports can be generated and provided regarding any health parameter that has been measured and recorded, such as weight, blood pressure and/or dosage compliance. The main control module can be programmed to provide these reports in a variety of formats, such as email or SMS text message, and through a variety of transmissions, such as wireless communication or API.

The main control module camera can also support the scan of medication information via OCR and other algorithms in order to facilitate and simplify the introduction of medication and dosage information into the PMHMS and/or external medications that can be integrated with the PMHMS.

Pill-Box Module.

The pill box module is a closed container that stores medication, typically in the form of pills. The pill box module comprises an LED numeric indicator that indicates the quantity of pills to be taken when the main control module indicates that is time to take a dose of the pills contained in the pill box module. Normally each pill box module stores one type of pill that the user retrieves when notified by an alarm from the main control module at the dosage amount indicated in the pill-box module LED display. The LED display in the pill box module ensures that the user is notified of the proper pill box module from which to take medication when the main control module indicates that medication should be taken.

The pill box modules each further comprise a programmable processor and memory in which information regarding the dosage of pills is stored and also the operation of closing and opening the lid to track the user's actions. The pill box modules further comprise a sensor that can detect when they are empty and display a warning or notice that they need to be refilled. The pill box modules may be provided in a pre-programmed state containing information on the dosage and dosage schedule of the pills contained within. The pill box modules communicate with the main control module and can transmit and receive information concerning dosage and dosage schedules. The main control module can maintain a master schedule of all pill box modules that are in communication at any one time.

In one embodiment, the pill box modules are stackable in a modular fashion which allows users to configure the size of the system as desired.

In one embodiment, the pill box module comprises two components: a pill box hub and a removable pill box enclosure. The pill box hub contains the display and all the electronics required for operation within the system and is connected to the distributed power and communication system in the same manner as the 1-component pill box module. For example, the pill box hub comprises a programmable processor and memory that stores information regarding the dosage of pills that are in the associated pill box enclosure. The pill box hub communicates with the main control module and can transmit and receive information concerning dosage and dosage schedules. The pill box hub comprises a cavity to house the pill box enclosure.

In this 2-component embodiment, the pill box enclosure is an air tight compartment that can accommodate medication typically in the form of pills. The pill box enclosure comprises an information storage device in the form of an RFID, barcode or any other form or technique that contains a unique identifier and additional information about the pills stored in the pill box enclosure, wherein the additional information may comprise the medicine name, dosing details or scheduling information. Where the pill box enclosure comprises an RFID, the pill box hub contains an RFID active scanner that can sense and read information programmed into the RFID which can then be transmitted to the main control module. Where the pill box enclosure comprises a barcode, the camera system of the PMHMS can scan the barcode and obtain the information from the pill box enclosure prior to inserting the pill box enclosure into the cavity of the pill box hub. The pill box enclosure further comprises a lid that is opened to obtain the medication contained inside. In one embodiment, the lid is hinged and is released to open by the pill box hub.

In operation, the pill box enclosure is inserted into the cavity of the pill box hub. The pill box hub contains a latching mechanism that keeps the pill box enclosure attached to the pill box hub. In addition, the pill box hub can detect if the lid of the pill box enclosure is open or closed.

In an embodiment, the pill box enclosure can be filled in a remote location and the medication information can be placed in the information storage device, wherein the additional information may comprise the medicine name, dosing details or scheduling information. The pill box enclosure is then inserted into the pill box hub, which retrieves the information stored in the pill box enclosure information storage device and transmits it to the main control module of the PMHMS.

The pill box enclosure can be a disposable unit that can be replaced once the medication in the pill box enclosure has been consumed or for any other purposes, for example sanitation reasons.

In an embodiment, the pill box hub controls the operation of the pill box enclosure lid by providing a mechanism that opens the pill box enclosure lid. While the user can directly close the pill box enclosure lid, the pill box hub prevents the user from opening the pill box enclosure lid directly. This action can only be taken by the mechanism in the pill box hub which is controlled by the main control module.

In one embodiment, the pill box hub prevents the user from opening the lid of the pill box enclosure by way of an electronically controlled lock that prevents the mechanism that allows the pill box enclosure lid to be opened from operating. A push lever comprising a lift section rotates when pressure is placed on the push lever to lift the pill box enclosure lid. A lid sensor is disposed on the push lever that can detect if the pill box enclosure lid has been opened and communicates that to the PMHMS. The lid sensor comprises an internal switch that is wired to the pill box hub. As the lid opens or closes, the internal switch opens or closes which is communicated from the pill box hub via the internal COM bus to the main control module. An extension of the push lever extends perpendicular from the bottom surface of the push lever which comprises an electronic locking device. If the electronic locking device is locked, the user cannot open the lid of the pill box enclosure. In one embodiment, the electronic locking device comprises a solenoid electric plunger that, when can commanded by the main control module, can extend a plunger into a hole in the push lever extension, thus mechanically locking the push lever to prevent the lid from opening. This electronic lock provides the PMHMS the ability of preventing the user from accessing the wrong medication by only allowing access to the correct pill box enclosure that contains the correct medication.

Modular Communication and Power Distribution.

The PMHMS comprises a distributed power and communication system that provides power to the various pill box and health parameter sensor modules. If a module such as a health parameter sensor module requires additional power, the health parameter sensor module can accommodate a separate entry point for external power as needed. The PMHMS also contains a distributed communications bus that propagates as pill box and health parameter sensor modules are added. The COM bus can support bidirectional communications between pill box and health parameter sensor modules and the main control module. With an API, the integration of various pill box modules and health parameter sensor modules into the PMHMS is simplified and automatic registration of such modules can be supported.

Sensor Modules.

The health parameter sensor modules contain sensors that allow the user to measure various physiological parameters. Exemplary health parameter sensor modules include heart rate, pulse oximetry and temperature, among others. The health parameter sensor modules integrate seamlessly into the PMHMS through the COM bus via an API. The health parameter sensor modules may or may not draw power from the distributed power system and may use external power. The health parameter sensor modules transfer information regarding health parameter readings to the main control module. Use of the health parameter sensor modules can be incorporated into the main control module master schedule, which may provide a visual indicator for the user to know that a particular health parameter reading should be taken.

Portable System.

The portable system is a smaller-sized unit that retains the capability of pill schedule management using both reduced profile pill box modules and health parameter sensor modules as does the full sized PMHMS. The portable system can interface to the main control module and download information such as the master schedule. In addition, the portable system can upload information back into the main control module. The portable system contains the same basic components of the full sized PMHMS: a main control module, pill box modules, health parameter sensor modules, and modular communication and power distribution. The portable system supports pill scheduling and health management but has a reduced physical layout for portability.

The portable system may be a single unit or it may be modular and expandable as needed or desired by the user. The portable system supports similar features as the full sized PMHMS. The pill box modules contain similar visual indicators as the pill box modules in the full sized PMHMS to ensure proper pill management. The health parameter sensor modules also support similar features as the health parameter sensor modules in the full size PMHMS.

Pill Management & Health Monitoring System with Universal Bottle Holder.

A universal bottle holder can be attached to the pill box modules which allows pill bottles to be mechanically placed in such a way that the pill bottles can be stored as part of the PMHMS. This facilitates proper filling of the pill box modules with the correct pills. The universal bottle holder can accommodate various sizes of pill bottles.

In operation, a user obtains a main control module and one or more pill box modules and/or health parameter sensor modules. The user connects the pill box modules and health parameter sensor modules to the main control module via the distributed power system which allows for bi-directional communication between main control modules and the other modules. The distributed power system also provides for provision of power to the modules.

In one embodiment, the pill box modules are each separately designated with unique identifiers by the programmable processor of the main control module. The user can program each pill box module from the main control module using the LCD display unit. For example, the user can set the dosage schedule and dosage amount of the pills in each pill box module. The main control module transmits information regarding the dosage and dosage schedule to the respective pill box modules, where the information is stored in the programmable processor of the pill box modules. When the time for a dose arrives according to a clock in the main control module, a visual and/or audible alarm is given notifying the user of the pill box module from which to take medicine. The pill box module associated with that dosage event can display on its LED display the number of pills to be taken, thus giving a visual display to take medication from that particular pill box module and also informing how many pills to take. The pill box module can detect if the module is opened and closed and transmit that information to the main control module where it can be stored and accessed to see if the user opened the pill box module at the dosage time. The pill box module can also contain a sensor that can detect when the pill box module is empty and provide an indicator that it needs to be refilled.

In one embodiment, the pill box module is supplied to the user filled with the medication and programmed as to the dosage schedule. When the pill box module is connected to the system, the main control module detects the presence of the pill box module and receives the information concerning dosage from that pill box module. The main control module creates a schedule for that pill box module and operates as previously described.

In one embodiment, one or more health parameter sensor modules are attached to the PMHMS in the same manner as the pill box modules. Each health parameter sensor module is designed to read information regarding a particular health parameter. For example, a blood pressure health parameter sensor module is programmed to detect and transmit blood pressure information to the main control module. Many health parameter sensor modules require that an external sensor be attached to the module to detect the health parameter. For example, the blood pressure health parameter sensor module would provide a connection for a cuff.

As for the medication dosage schedules, the main control module can be programmed to remind the user to measure various health parameters.

The various health parameter sensor modules are manufactured for use with particular external sensors. The main control module can receive programming information from the health parameter sensor modules to set up and maintain data on the health parameters for that particular health parameter sensor module. In one embodiment, the main control module can detect the particular health parameter sensor external device that will be used with a particular health parameter sensor module and access the Internet over the second communications link to download programming information or update programming information.

The main control module provides power to the health parameter sensor modules, but in some cases additional power may be needed in which case the particular health parameter sensor module can allow for input of external power.

By providing modular connectivity and bi-directional communication, the system is infinitely customizable for a user, and also easily changed according to the user's changing needs.

Turning to the figures, FIG. 1 depicts a PMHMS 100 having a main control module 110 comprising a display 105, a visual reminder 115, an audio device 117 that may comprise a microphone and/or a speaker, a camera 111, a wired external communications link 112, a wireless communications link 113; and three pill box modules 120 each having a lid 125 and an LED display 135 in each lid 125. Information on dosage schedule or other information, including the time, may be displayed in the display 105 of the main control module 110. The LED display 135 in the lid 125 of each pill box module 120 displays the number of pills to be taken from that pill box module 120 according to the dosage schedule.

Figure 2:
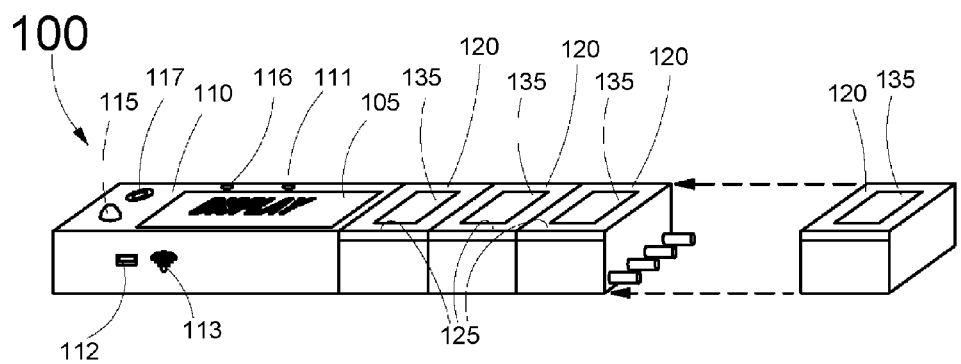
FIG. 2 depicts the addition or removal of a fourth pill box module to the system depicted in FIG. 1.

FIG. 2 depicts the addition or removal of a fourth pill box module 120 to the PMHMS 100 depicted in FIG. 1.

Figure 3:
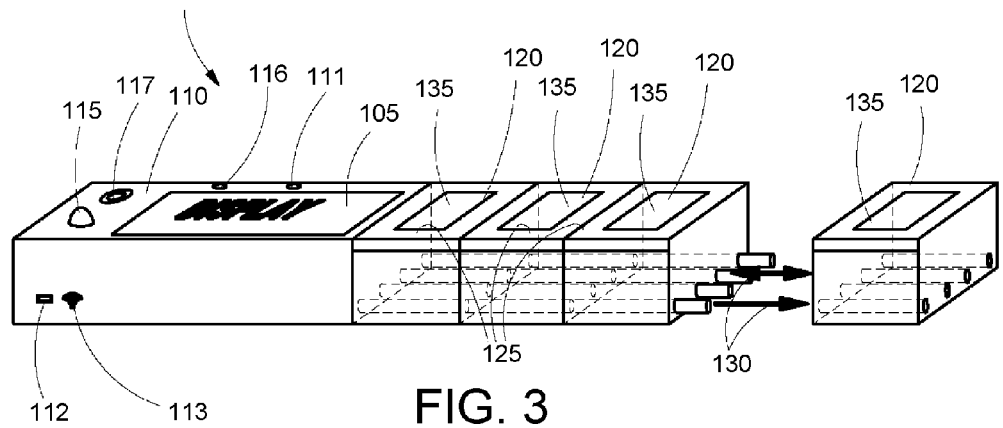
FIG. 3 depicts the power and communication connections between the main control module and the other modules.

FIG. 3 depicts power and communication connections 130 allowing power to flow from the main control module 110 to the pill box modules 120, and for communication to flow in a bi-directional manner between the main control module 110 and the pill box modules 120 of the PMHMS 100.

Figure 4:
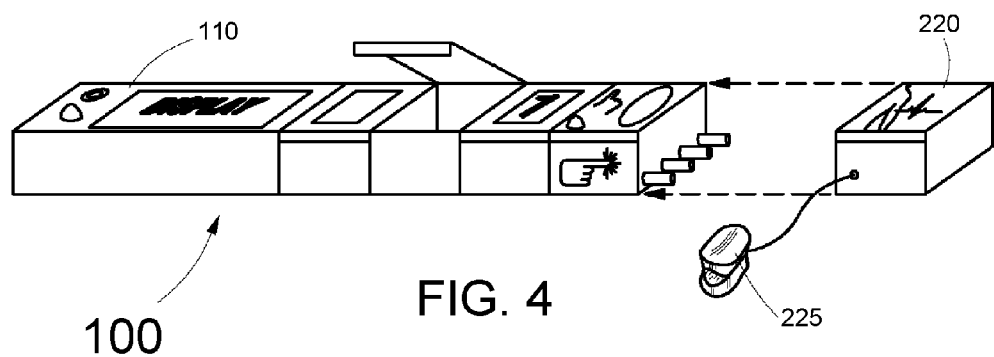
FIG. 4 depicts a health parameter sensor module being connected to the system.

FIG. 4 depicts a health parameter sensor module 220 being connected to the PMHMS 100. The health parameter module 220 shown in FIG. 4 comprises an external sensor 225 for measuring a biometric sensor that can be used for security or confirmation that the right person took the medication, and also a pulse oximetry sensor (measuring heart rate and oxygen saturation.

Figure 5:
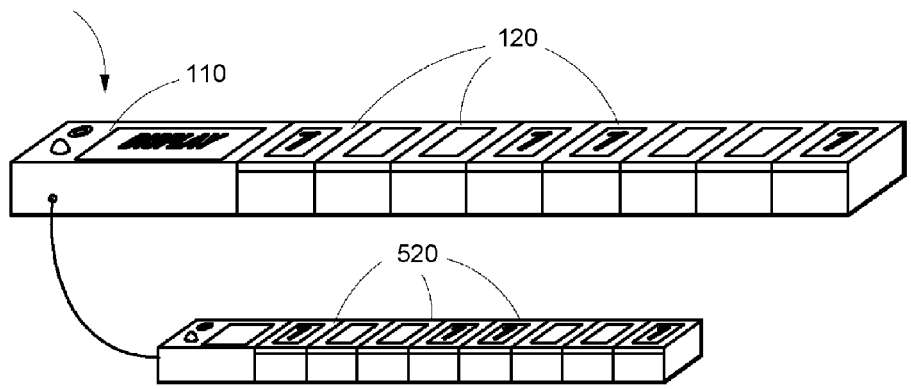
FIG. 5 depicts a portable system as it is connected to the main control module to download or upload information.
Figure 6:
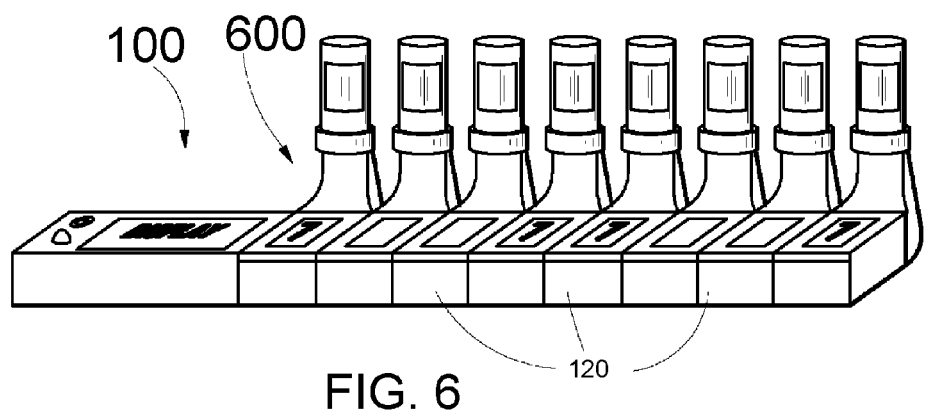
FIG. 6 depicts a universal bottle holder attached to the pill box modules of the system.

FIG. 5 depicts a portable system 500 as it is connected to the main control module 110 of the full-sized PMHMS 100 to download or upload information. The portable system 500 comprises pill box modules 520 as shown that operate in the same manner as the pill box modules 120 of the full sized PMHMS 100. Health parameter sensor modules (not shown) can also be added to the portable system 500. FIG. 6 depicts a universal bottle holder 600 attached to the pill box modules 120 of the PMHMS 100.

Figure 7:
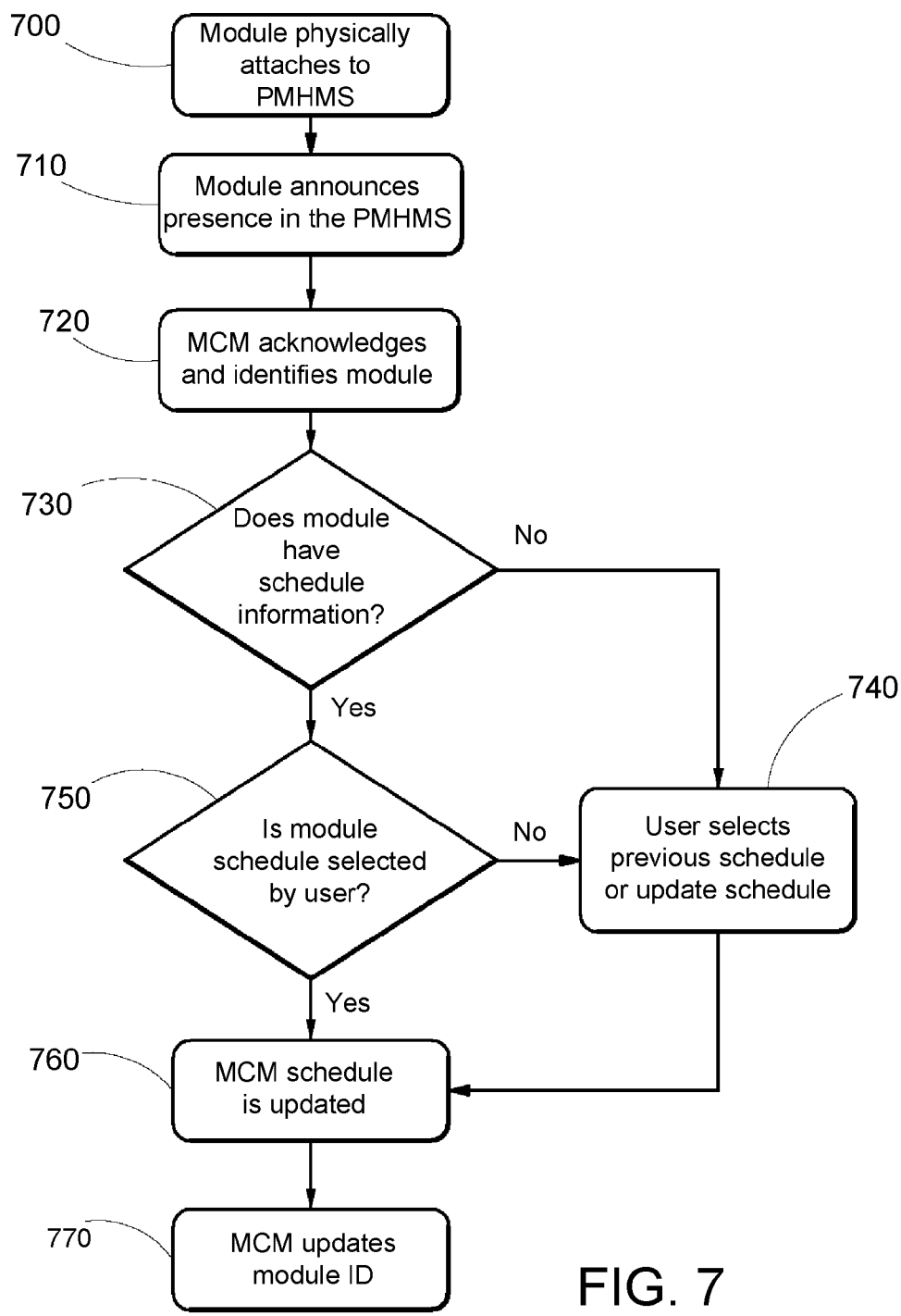
FIG. 7 depicts the initialization process for the main control module.

FIG. 7 depicts the initialization process for the main control module (MDM). At 700, a module such as a pill box module is physically connected to the PMHMS, whereupon at 710 the pill box module sends a communication to the main control module. At 720, the main control module acknowledges the presence of the pill box module and identifies the pill box module. If at 730 the module does not contain pre-programmed scheduling information, at 740 the user selects a previous schedule or manually enters scheduling information at the display of the main control module. At 760, the main control module is updated with the manually entered information or the selected previous schedule. If at 730 the module is determined to contain pre-programmed information, at 750 the user may select the pre-programmed schedule and at 760 the main control module is updated with the pre-programmed schedule. If at 750 the user does not select the pre-programmed schedule, at 740 the user selects a previous schedule or manually enters scheduling information at the display of the main control module. At 760, the main control module is updated with the manually entered information or the selected previous schedule. At 770 the main control module queries the module for its unique ID and, if necessary, updates the module ID stored in the main control module.

Figure 8:
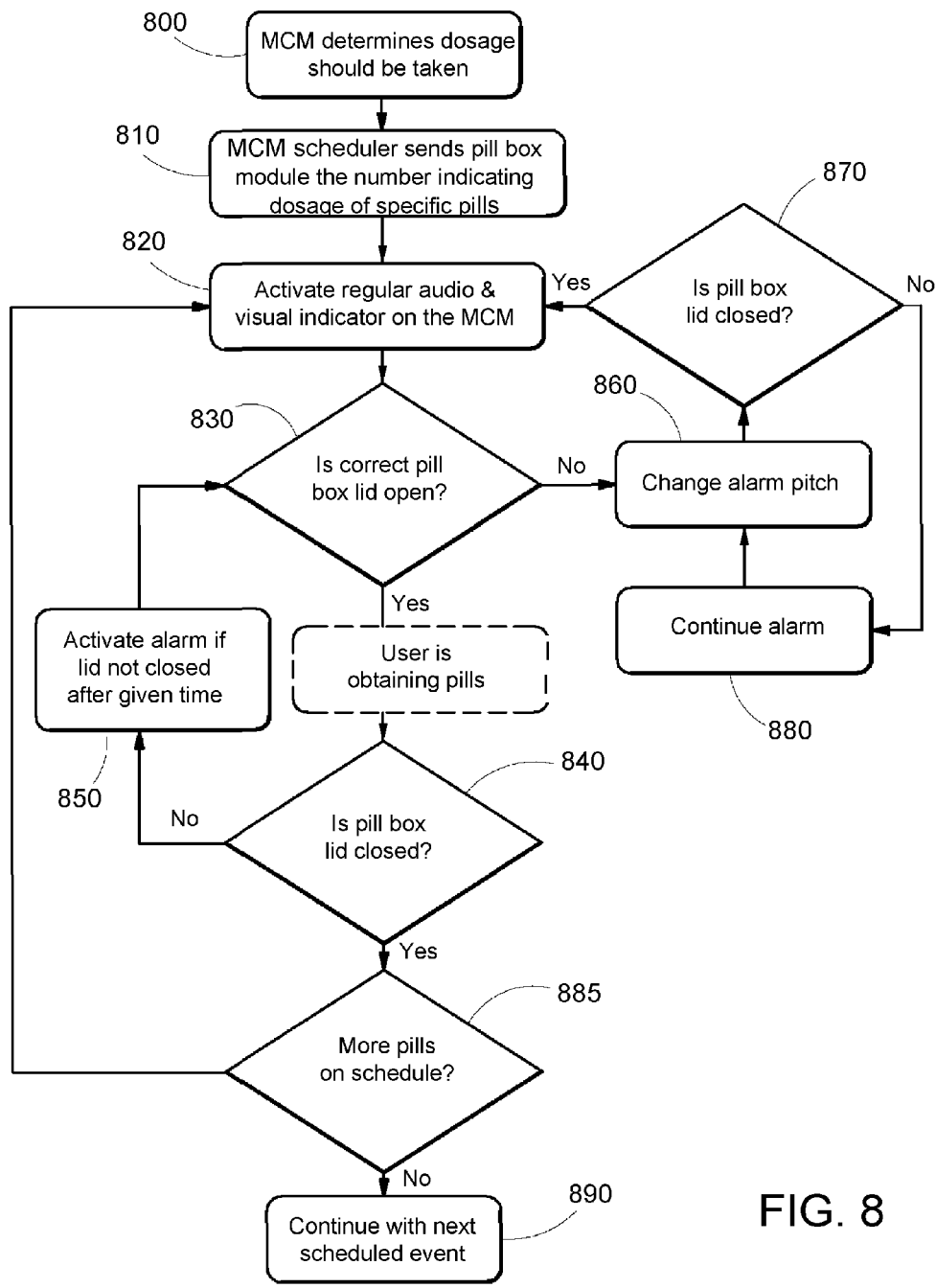
FIG. 8 depicts the flow-scheme for setting the schedule for a pill box module.

In FIG. 8, at Step 800, the main control module determines according to the schedule selected in FIG. 7 that a dosage should be taken. At Step 810, the main control module schedule transmits to the pill box module the number of pills to be taken in a dosage to be displayed on the pill box module LED display. At Step 820, at the scheduled dosage time for the medication in that particular pill box module, the main control module scheduler activates audio and visual indicators on the display of the main control module to alert the user that it is time to take medication from that pill box module. At Step 830, if the correct pill box module lid is opened by the user of the PMHMS, the main control module schedule assumes that the user is accessing the correct pills for that particular dosage. At Step 840, if that pill box module lid is not thereafter closed within a given interval, then at Step 850 an alarm will be triggered to remind the user to close the lid of the pill box module. At Step 830, if the incorrect pill box module lid is opened, then at Step 860 there will be an alarm with a different pitch than the reminder alarm to alert the user that an incorrect pill box module has been accessed. At Step 870, if the incorrect pill box lid remains open after a predetermined amount of time, at Step 880, the alarm will continue; at Step 870, if the incorrect pill box lid is thereafter closed, the alarm will stop. At Step 820, the main control module scheduler activates audio and visual indicators on the display of the main control module to alert the user that it is time to take medication from that pill box module and at Step 830, if the correct pill box module lid is opened by the user of the PMHMS, the main control module schedule assumes that the user is accessing the correct pills for that particular dosage. At step 840, once the correct pill box module has been accessed and the lid is closed, at Step 885 the main control module scheduler determines that more dosage events remain on the schedule within a predetermined amount of time for that pill box module, at Step 820 the process for the next dosage from that pill box module initiates. If at Step 885 the main control module scheduler determines that no more pills from that pill box module are scheduled to be taken within a predetermined amount of time, at Step 890 the main control module continues with the next scheduled event.

Figure 9:
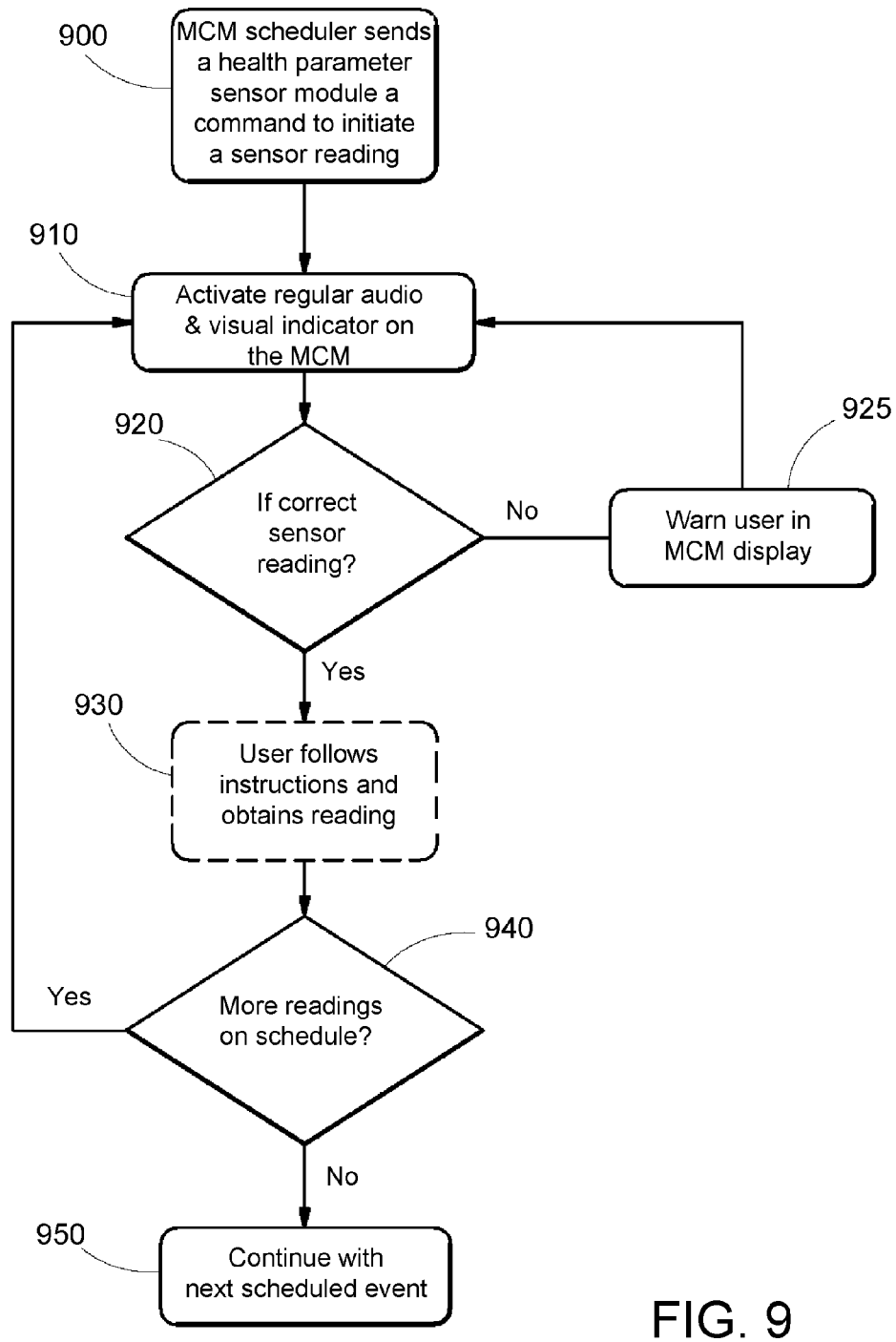
FIG. 9 depicts the flow-scheme for setting the schedule for a health parameter sensor module.

FIG. 9 depicts a flow-scheme of the sensor scheduler process for health parameter sensor modules. When a health parameter sensor module is connected to the PMHMS, it is initialized and a schedule for taking readings is set by the main control module in a similar manner as set forth in FIG. 7 for a pill box module. At Step 900, the main control module scheduler sends a command at the scheduled time to initiate a health parameter sensor reading. At Step 910, the main control module provides an audible and/or visual alarm to remind the user to take the reading. At Step 920, the main control module determines if the correct sensor is being accessed by the user. If the user selects the wrong sensor module, then at Step 925 the main control module provides a warning to the user in its display. If at Step 920, the main control module detects that the user has accessed the correct health parameter sensor, then at Step 930, the user follows instructions and obtains the reading(s) from the sensor. Once the health parameter sensor readings are obtained and stored in the memory of the main control module then in Step 940 the scheduler assesses if additional readings are scheduled within a predetermined amount of time. If no more readings are scheduled within that predetermined amount of time, then at Step 950 the main control module continues with the next scheduled event.

Figure 10:
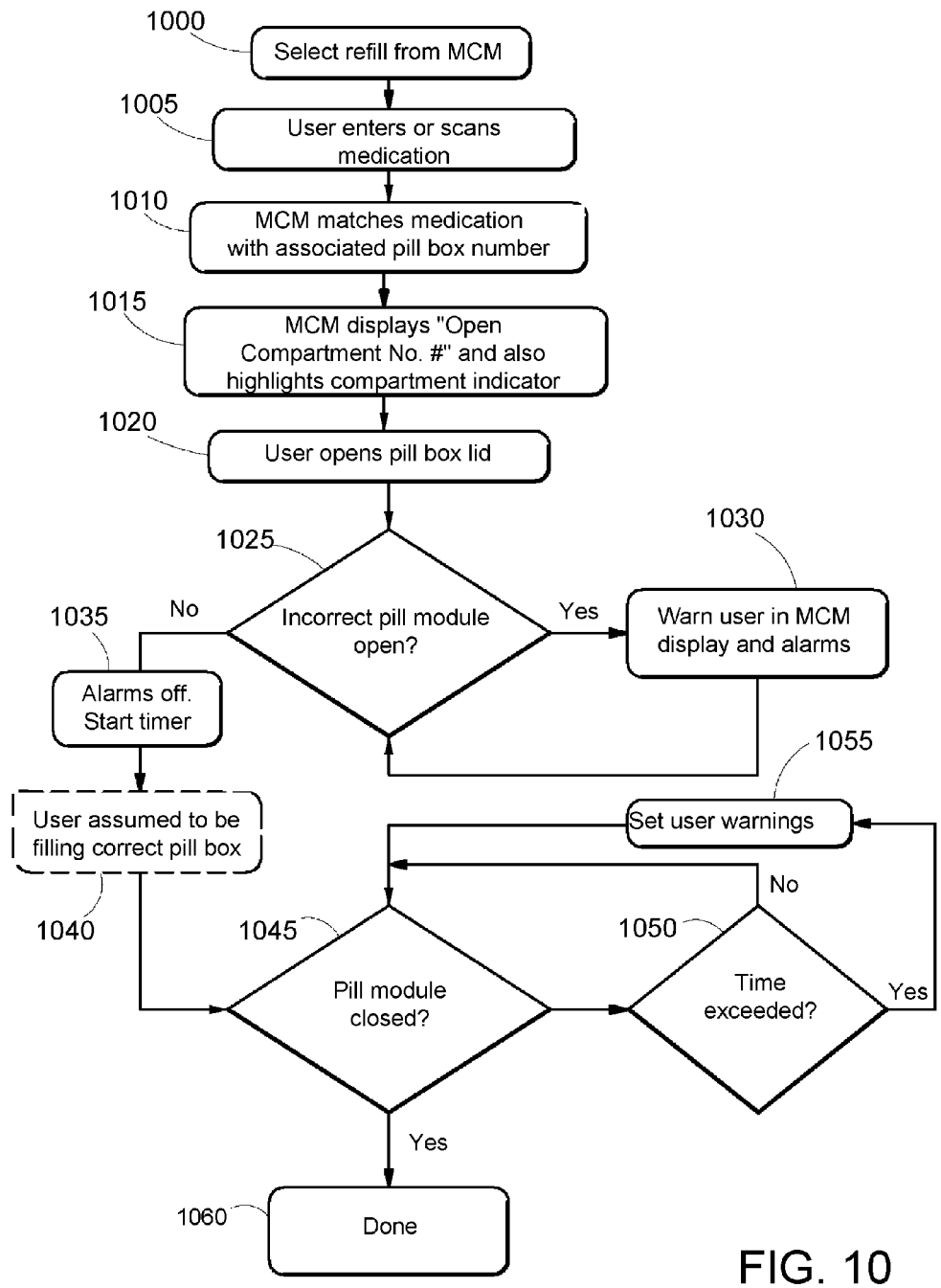
FIG. 10 depicts the flow-scheme for the refill process of a pill box module.

FIG. 10 depicts the flow-scheme of the refill process of a pill box module. At Step 1000, the user selects the option of "Refill" on the display of the main control module either directly or by accessing the main control module by an external device. At Step 1005, the user either enters the medication name or scans the medication information into the main control module. At Step 1010, the medication to be refilled is matched with a specific pill box module by a unique identifier and the main control module allows the user the option to open the lid for that pill box module. At Step 1015, the main control module display provides a message to the user to open the pill box module. At Step 1020, the user opens the pill box module lid. At Step 1025, the main control module determines if the correct pill box module lid has been opened. If not, at Step 1030, the main control module provides an audible and/or visual alarm. If at Step 1025 the correct pill box module lid is opened, then at Step 1035 a timer begins monitoring the amount of time that the pill box module lid is open according to a predetermined time that has been determined sufficient to refill the pill box module with the medication. At Step 1040, the user is assumed to be refilling the correct pill box container. At Step 1045, the main control module determines if the pill box module lid has been closed. If at Step 1050 the pill box module lid remains open past the predetermined amount of time to fill within the predetermined time, then at Step 1055 the main control module initiates user warnings that may comprise audio sounds and visual indicators. Once the pill box module lid is determined to be closed, at Step 1060 the refill process is assumed to be complete and the main control module continues to the next scheduled event.

Figure 11:
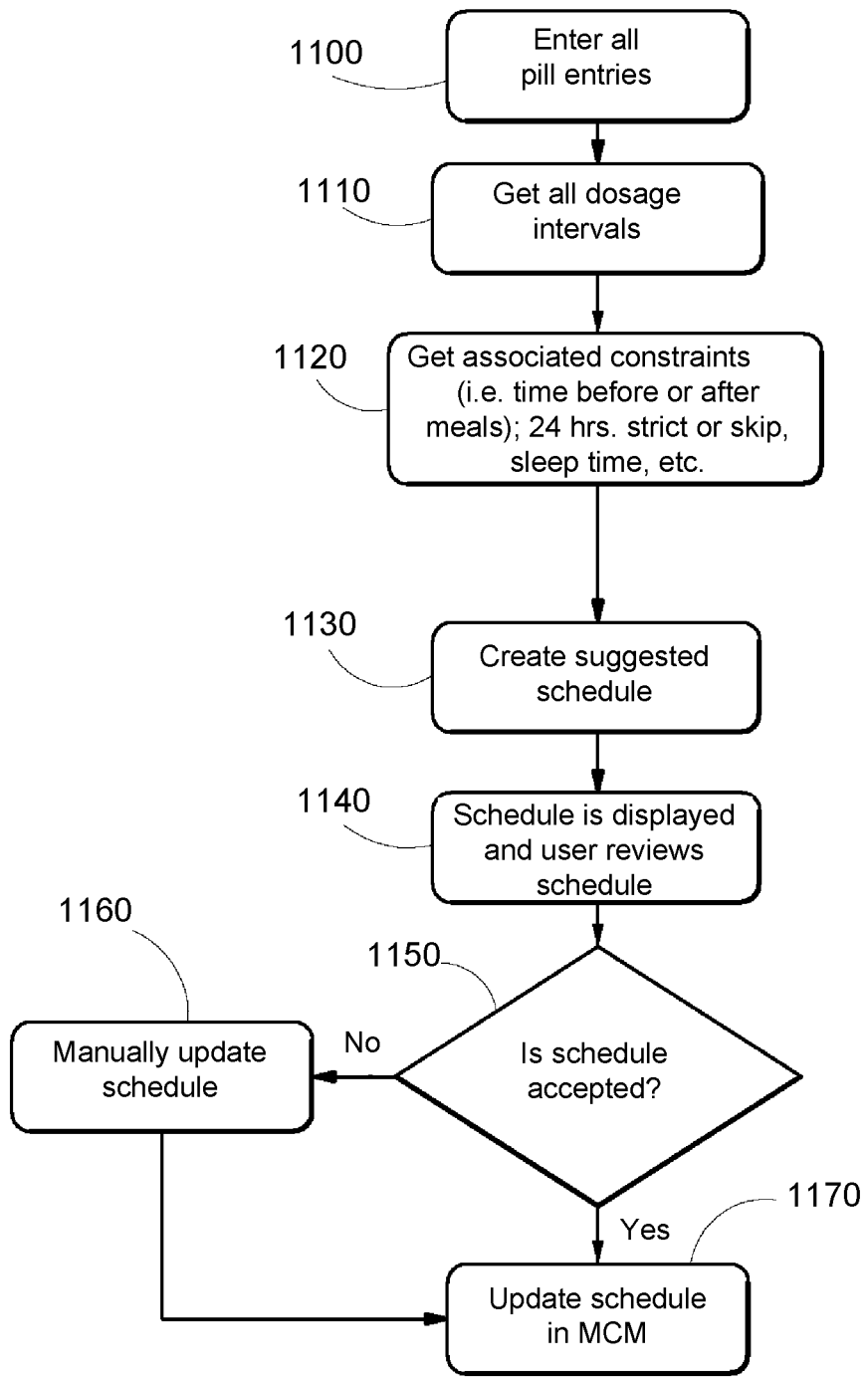
FIG. 11 depicts the flow-scheme for setting a suggested schedule by the main control module.

FIG. 11 depicts the flow-scheme for deriving a suggested schedule by the main control module based on the patient's input. At Step 1100, the user enters information regarding pill dosages into the main control module. At Step 1110, the main control module determines dosage intervals for a particular medication. At Step 1120, the main control module determines all constraints for that particular medication. At Step 1130, the main control module algorithm computes a suggested dosage schedule according to the user inputs at Step 1100. At Step 1140, the suggested schedule is displayed on the display of the main control module and the user reviews the suggested schedule. At Step 1150, the user can decide to accept or reject the suggested schedule. At Step 1160, if the user rejects the suggested schedule, he/she makes changes and at Step 1170 the revised schedule is stored in the main control module. If at Step 1150 the user accepts the suggested schedule, the suggested schedule is stored in the main control module.

Figure 12:
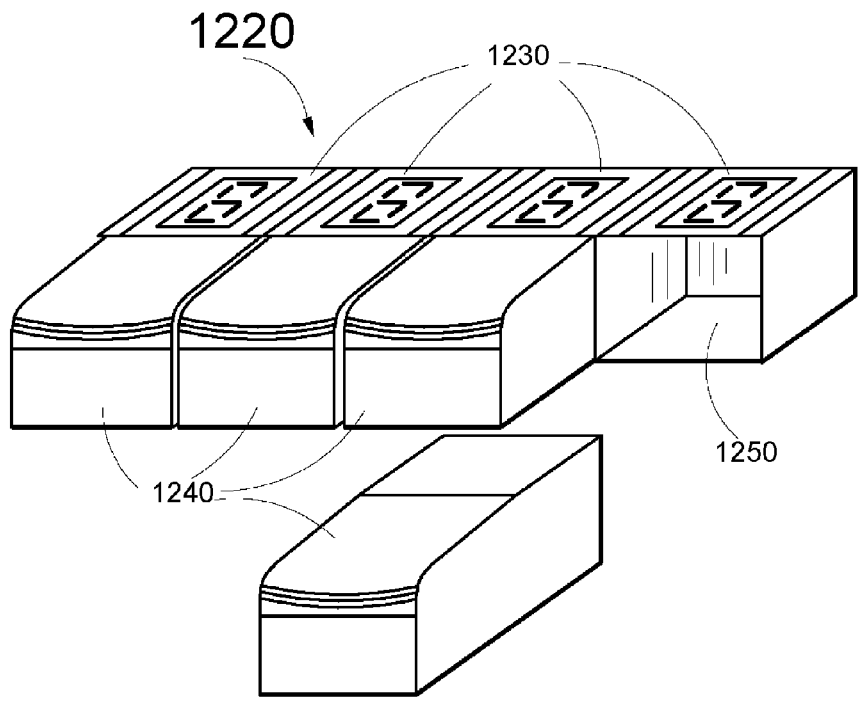
FIG. 12 depicts a plurality of 2-component pill box modules each comprising a pill box hub and a pill box enclosure in detachable connection according to one embodiment of the invention.

FIG. 12 depicts a plurality of 2-component pill box modules 1220 each comprising a pill box hub 1230 and a pill box enclosure 1240 in detachable connection according to one embodiment of the invention. Cavity 1250 of pill box hub 1230 that houses pill box enclosure 1240 is also shown.

Figure 13:
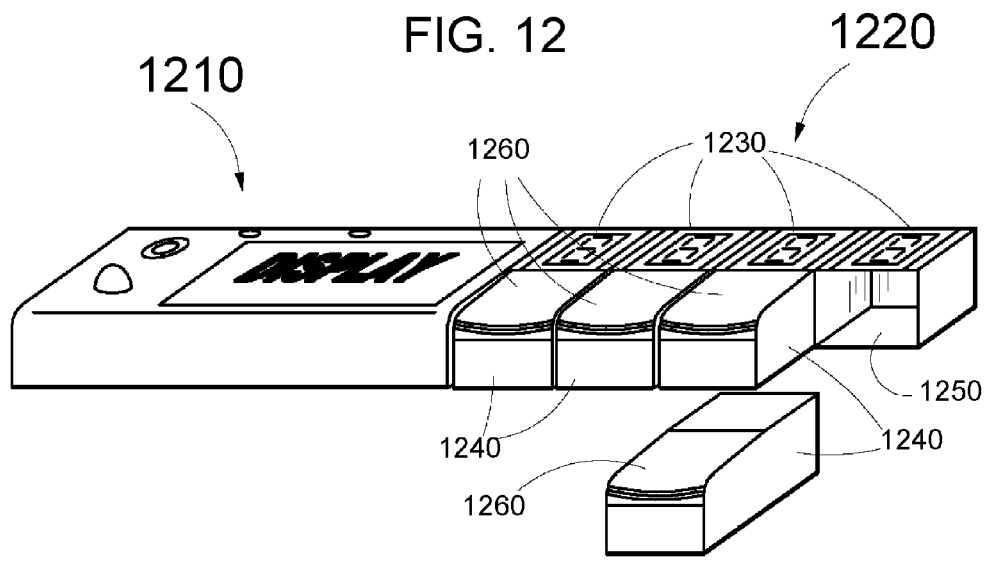
FIG. 13 depicts a plurality of 2-component pill box modules each comprising a pill box hub and a pill box enclosure attached to the main control module in detachable connection according to one embodiment of the invention

FIG. 13 depicts a plurality of 2-component pill box modules 1220 each comprising a pill box hub 1230 and a pill box enclosure 1240 attached to the main control module 1210 in detachable connection according to one embodiment of the invention that allows for opening of the pill box enclosure lid 1260 to be controlled from the pill box hub 1220.

Figure 14:
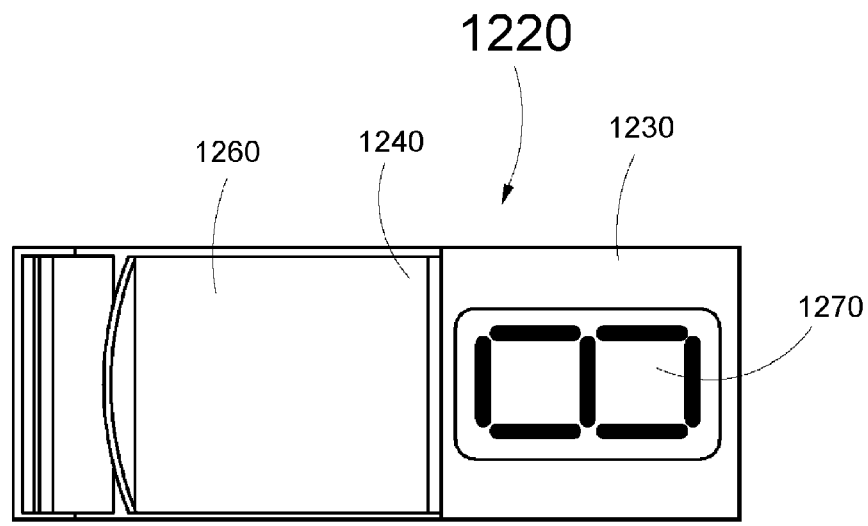
FIG. 14 depicts a top view of the internal latch of the pill box hub.

FIG. 14 depicts a top view of a 2-component pill box module 1220 showing an LED display 1270; the lid 1260; and the pill box hub 1230.

Figure 15:
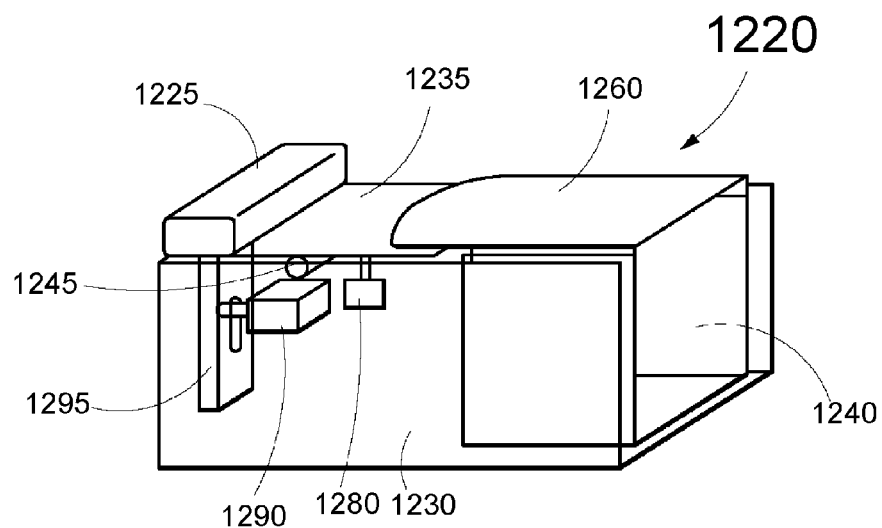
FIG. 15 depicts a left side perspective view of a 2-component pill box module each comprising a pill box hub and a pill box enclosure.

FIG. 15 depicts a left side cutout perspective view of one embodiment of the pill box enclosure 1240 and pill box hub 1230. Pill box hub 1230 further comprises a push lever 1225 and a lift section 1235 that rotates around post 1245 when pressure is placed on push lever 1225, lifting pill box enclosure lid 1260 if the push lever extension 1295 is not locked by the electronic locking device 1290. Pill box hub 1230 further comprises a lid sensor 1280 that detects when lid 1260 has been opened or closed.

Figures 16A, 16B:
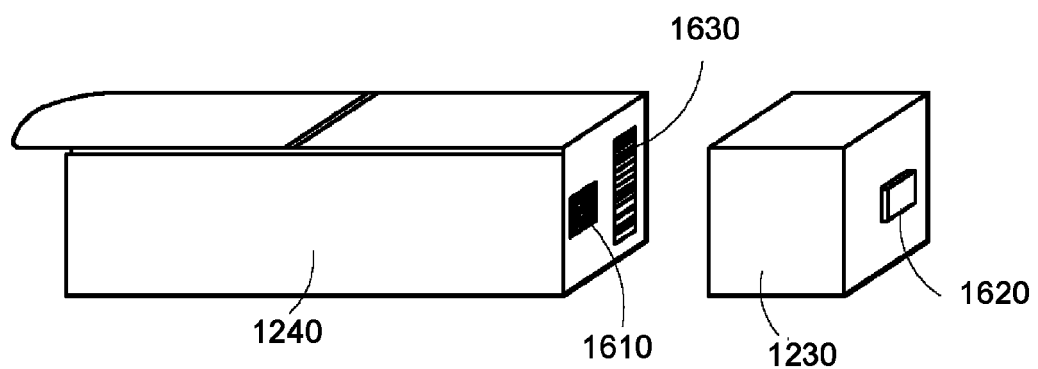
FIG. 16a depicts a pill box enclosure having a plurality of readable memory and FIG. 16b depicts a pill box module having a readable memory.

FIG. 16a depicts a pill box enclosure 1240 with a readable RFID memory 1610 and a second readable memory 1630 comprising a barcode, where the barcode can be read by the main control module camera. FIG. 16b depicts a pill box hub 1230 having an RFID reader 1620 capable of extracting the information from the RFID memory 1610.

The foregoing embodiments have been presented for the purpose of illustration and description only and are not to be construed as limiting the scope of the invention in any way. The scope of the invention is to be determined from the claims appended hereto.

What is claimed is:

1. A modular medication dosage control and health monitoring device comprising:
   a main control module; and
   one or more pill box modules,
   wherein the main control module is connected to the pill box modules via a distributed power and communication system, wherein the distributed power and communication system facilitates modular bi-directional communication between the main control module and each of the pill box modules,
   wherein the main control module provides power to the pill box modules via the distributed power and communication system,
   wherein the distributed power and communication system comprises a DC power bus which directly provides DC power to the pill box modules,
   wherein the distributed power and communication system comprises a wired communications link that facilitates modular bi-directional communications between the main control module and each of the pill box modules,
   wherein the main control module and each pill box module comprises a rewriteable memory and a programmable processor, wherein the main control module programmable processor is in modular bi-directional communication with each individual pill box module, wherein further main control module programmable processor assigns a unique identifier to each pill box module, wherein the main control module programmable processor further comprises a pill box module scheduler that stores a dosage schedule for each separate pill box module in its rewriteable memory that is identified with each pill box module unique identifier, wherein the dosage schedule is stored in the programmable processor of each separate pill box module;
   wherein the main control module further comprises a clock;
   wherein the main control module further comprises a display that allows programming of the programmable processor by a user of the device;
   wherein the main control module further comprises a first communications link for communication over a local area network;
   wherein each pill box module comprises an LED display under control of the pill box module programmable processor;
   wherein the pill box modules are separately detachable from the device.

2. The device of claim 1, further comprising one or more health parameter sensor modules connected to the main control module via the distributed power and communication system.

3. The device of claim 2, wherein one or more health parameter sensor modules comprises a sensor unit.

4. The device of claim 1, wherein the main control module further comprises a second communications link for communication over a network.

5. The device of claim 1, wherein the main control module can be accessed by an external device over a communications network.

6. The device of claim 4, wherein the main control module can be accessed by the external device over the second communications link.

7. The device of claim 1, wherein each pill box module contains a dosage schedule prior to connection to the main control module, wherein upon connection to the main control module the programmable processor of each pill box modules transmits the dosage schedule to the main control module, whereupon the dosage schedule is stored in the pill box module scheduler.

8. The device of claim 1, wherein the user programs the dosage schedule for each pill box module via the display of the main control module.

9. The device of claim 1, wherein the pill box module comprises a pill box hub and a pill box enclosure, wherein the pill box hub comprises an internal cavity into which the pill box enclosure is removably inserted, wherein the pill box hub comprises an LED display and the rewritable memory and programmable processor, wherein each pill box hub is separately in communication with the main control module through the distributed power and communication system, wherein each pill box hub receives power over the distributed power and communication system, wherein each pill box enclosure comprises a readable memory, wherein each pill box hub reads the information stored in the readable memory of the pill box enclosure and can transmit that information to the main control module, wherein each pill box enclosure contains medication.

10. The device of claim 9, wherein the readable memory of each pill box enclosure comprises an information storage device.

11. The device of claim 10, wherein the information storage device comprises an RFID chip, an integrated circuit chip, a QR code, a 2-dimensional tag, a 3-dimensional tag or a barcode.

12. The device of claim 10, wherein the readable memory of each pill box enclosure contains information relating to the medication stored in the pill box enclosure.

13. The device of claim 10, wherein each pill box enclosure is filled with medication by someone other than the user of the device.

14. The device of claim 13, wherein upon attachment of each pill box enclosure to the pill box hub, medication information is read by the pill box enclosure and transmitted to the main control module, whereupon the main control module assigns a unique identifier to each pill box enclosure and pill box hub, whereupon if the information comprises a dosage schedule that dosage schedule is stored in the pill box module scheduler of the main control module.

15. The device of claim 1, wherein the device comprises a camera, audio output and a microphone that supports video conferencing via the second communications link.

16. The device of claim 15, wherein the camera comprises a scanner, wherein information scanned by the scanner is entered into the main control module.

17. The device of claim 16, wherein the scanner comprises capability to conduct OCR on information scanned by the camera, read a QR code, read a 2-dimensional tag, read a 3-dimensional tag or read a barcode.

18. The device of claim 1, wherein the main control module develops a schedule based on input into the main control module display by the user of information relating to the medication, the information relating to the medication comprising dosage information and constraints relating to the medication.

19. The device of claim 1, wherein the main control module records information regarding medications removed from each pill box module.

* * * * *